United States Patent
Rogers et al.

(10) Patent No.: US 8,834,650 B2
(45) Date of Patent: *Sep. 16, 2014

(54) MEDICAL IMPLEMENT CLEANING DEVICE

(71) Applicant: Ivera Medical Corporation, San Diego, CA (US)

(72) Inventors: Bobby E. Rogers, San Diego, CA (US); Paul DiPerna, San Clemente, CA (US)

(73) Assignee: Ivera Medical Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/107,458

(22) Filed: Dec. 16, 2013

(65) Prior Publication Data
US 2014/0101876 A1    Apr. 17, 2014

Related U.S. Application Data

(63) Continuation of application No. 13/466,976, filed on May 8, 2012, which is a continuation of application No. 13/189,457, filed on Jul. 22, 2011, now Pat. No. 8,206,514, which is a continuation of application No. 12/860,825, filed on Aug. 20, 2010, now Pat. No. 7,985,302, which is a continuation of application No. 11/705,805, filed on Feb. 12, 2007, now Pat. No. 7,780,794.

(60) Provisional application No. 60/832,437, filed on Jul. 21, 2006, provisional application No. 60/850,438, filed on Oct. 10, 2006.

(51) Int. Cl.
*B08B 3/08* (2006.01)
*B08B 11/02* (2006.01)
*B08B 1/00* (2006.01)
*A61L 2/18* (2006.01)
*A61B 19/00* (2006.01)

(52) U.S. Cl.
CPC .. *A61B 19/34* (2013.01); *A61L 2/18* (2013.01)
USPC ..... 134/115 R; 134/201; 15/97.1; 15/104.92; 15/104.93

(58) Field of Classification Search
USPC ............ 15/97.1, 104.92, 104.93, 104.94
See application file for complete search history.

(56) References Cited

U.S. PATENT DOCUMENTS

1,744,026 A    1/1930    Baltzley
1,841,597 A    1/1932    Hammer et al.
(Continued)

FOREIGN PATENT DOCUMENTS

DE    2164821 A1    8/1972
EP    0462355 A1    12/1991
(Continued)

OTHER PUBLICATIONS

U.S. Appl. No. 60/815,806, filed Jun. 22, 2006, Anderson et al.
(Continued)

*Primary Examiner* — Michael Kornakov
*Assistant Examiner* — Natasha Campbell
(74) *Attorney, Agent, or Firm* — Mintz Levin Cohn Ferris Glovsky and Popeo, P.C.

(57) ABSTRACT

A system for cleaning a site of a medical implement is disclosed. The system can include a strip of flexible material and a plurality of cleaning devices attached to the strip. Each cleaning device can include a cap, one or more protrusions, and a cleaning agent. The cap can be selectively removable from the strip of flexible material and can have an inner cavity that is sealed when the cleaning device is attached to the strip and unsealed upon removal of the cleaning device from the strip. The inner cavity can receive a site of the medical implement. The one or more protrusions can extend inwardly from the inner cavity and can engage corresponding protrusions on the site of the medical implement. The cleaning agent can occupy at least some of the inner cavity and can be formulated to clean the site of the medical implement.

10 Claims, 7 Drawing Sheets

(56) References Cited

U.S. PATENT DOCUMENTS

| | | | |
|---|---|---|---|
| 1,937,492 A | 11/1933 | Merolle |
| 2,341,285 A | 2/1944 | Petrullo |
| 2,731,963 A | 1/1956 | Blank |
| 2,740,480 A | 4/1956 | Cox et al. |
| 2,993,612 A | 7/1961 | Trautvetter |
| 3,120,879 A | 2/1964 | Warner |
| 3,362,587 A | 1/1968 | Postel et al. |
| 3,391,847 A | 7/1968 | Christine et al. |
| 3,405,831 A | 10/1968 | Hudson et al. |
| 3,431,548 A | 3/1969 | Busier et al. |
| 3,435,978 A | 4/1969 | Wittwer |
| 3,443,686 A | 5/1969 | Raymond et al. |
| 3,651,972 A | 3/1972 | Itoh |
| 3,771,685 A | 11/1973 | Micallef |
| 3,818,627 A | 6/1974 | Lebensfeld |
| 3,979,001 A | 9/1976 | Bogert |
| 3,987,921 A | 10/1976 | Aichinger |
| 4,089,463 A | 5/1978 | Babiol |
| 4,169,751 A | 10/1979 | Yen |
| 4,257,526 A | 3/1981 | Weits et al. |
| 4,280,632 A | 7/1981 | Yuhara |
| 4,289,248 A | 9/1981 | Lynn |
| 4,340,148 A | 7/1982 | Beckham |
| 4,401,227 A | 8/1983 | Pehr |
| 4,440,207 A | 4/1984 | Genatempo et al. |
| 4,461,394 A | 7/1984 | Sendel et al. |
| 4,564,116 A | 1/1986 | Prohaska |
| 4,572,373 A | 2/1986 | Johansson |
| 4,597,758 A | 7/1986 | Aalto et al. |
| 4,671,306 A | 6/1987 | Spector |
| 4,674,643 A | 6/1987 | Wilde et al. |
| 4,712,705 A | 12/1987 | Fuehrer |
| 4,752,983 A | 6/1988 | Grieshaber |
| 4,778,447 A | 10/1988 | Velde et al. |
| 4,798,303 A | 1/1989 | Arnold |
| 4,991,629 A | 2/1991 | Ernesto et al. |
| 5,078,693 A | 1/1992 | Shine |
| 5,143,104 A | 9/1992 | Iba et al. |
| 5,169,033 A | 12/1992 | Shay |
| 5,184,742 A | 2/1993 | DeCaprio et al. |
| 5,242,425 A | 9/1993 | White et al. |
| 5,263,606 A | 11/1993 | Dutt et al. |
| 5,292,020 A | 3/1994 | Narin |
| 5,385,372 A | 1/1995 | Utterberg |
| 5,385,378 A | 1/1995 | Hakamada et al. |
| 5,398,837 A | 3/1995 | Degrassi |
| 5,445,270 A | 8/1995 | Dratz |
| 5,554,135 A | 9/1996 | Menyhay |
| 5,702,017 A | 12/1997 | Goncalves |
| 5,743,884 A | 4/1998 | Hasson et al. |
| 5,792,120 A | 8/1998 | Menyhay |
| 5,951,519 A | 9/1999 | Utterberg |
| 5,954,957 A | 9/1999 | Chin-Loy et al. |
| 6,004,299 A | 12/1999 | Arai et al. |
| 6,045,539 A | 4/2000 | Menyhay |
| 6,102,223 A | 8/2000 | Montgomery |
| 6,116,468 A | 9/2000 | Nilson |
| 6,227,391 B1 | 5/2001 | King |
| 6,250,315 B1 | 6/2001 | Ernster |
| 6,364,862 B1 | 4/2002 | Bonilla |
| 6,523,686 B1 | 2/2003 | Bae |
| 6,527,751 B2 | 3/2003 | Fischer et al. |
| 6,622,882 B2 | 9/2003 | Smith |
| 6,913,157 B2 | 7/2005 | Oh |
| 7,188,623 B2 | 3/2007 | Anderson et al. |
| 7,282,186 B2 | 10/2007 | Lake, Jr. et al. |
| 7,329,235 B2 | 2/2008 | Bertron et al. |
| 7,427,275 B2 | 9/2008 | DeRuntz et al. |
| 7,500,964 B2 | 3/2009 | Shaw et al. |
| 7,682,561 B2 | 3/2010 | Davis et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,931,618 B2 | 4/2011 | Wyrick |
| 7,931,877 B2 | 4/2011 | Steffens et al. |
| 7,967,779 B2 | 6/2011 | Bertron et al. |
| 7,985,302 B2 | 7/2011 | Rogers et al. |
| 7,988,676 B1 | 8/2011 | Gray |
| 8,061,544 B2 | 11/2011 | Frishman |
| 8,105,293 B2 | 1/2012 | Pickhard |
| 8,162,899 B2 | 4/2012 | Tennican |
| 8,167,847 B2 | 5/2012 | Anderson et al. |
| 8,172,813 B2 | 5/2012 | Janish |
| 8,177,768 B2 | 5/2012 | Leinsing |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,277,422 B2 | 10/2012 | Oliver et al. |
| 8,287,491 B2 | 10/2012 | Burns et al. |
| 8,296,893 B2 | 10/2012 | Vinci et al. |
| 8,303,548 B2 | 11/2012 | Ito et al. |
| 8,641,681 B2 | 2/2014 | Solomon et al. |
| 8,647,326 B2 | 2/2014 | Solomon et al. |
| 2002/0133124 A1 | 9/2002 | Leinsing et al. |
| 2004/0024357 A1 | 2/2004 | Pelkey et al. |
| 2004/0030321 A1 | 2/2004 | Fangrow |
| 2004/0039341 A1 | 2/2004 | Ranalletta |
| 2004/0195136 A1 | 10/2004 | Young et al. |
| 2004/0258560 A1 | 12/2004 | Lake et al. |
| 2005/0147524 A1 | 7/2005 | Bousquet |
| 2005/0147525 A1 | 7/2005 | Bousquet |
| 2005/0214185 A1 | 9/2005 | Castaneda |
| 2006/0030827 A1 | 2/2006 | Raulerson et al. |
| 2006/0048313 A1 | 3/2006 | Yamaki |
| 2007/0112333 A1 | 5/2007 | Hoang et al. |
| 2008/0019889 A1 | 1/2008 | Rogers et al. |
| 2008/0086091 A1 | 4/2008 | Anderson et al. |
| 2008/0132880 A1 | 6/2008 | Buchman |
| 2008/0177250 A1 | 7/2008 | Howlett et al. |
| 2009/0028750 A1 | 1/2009 | Ryan |
| 2009/0099529 A1 | 4/2009 | Anderson et al. |
| 2009/0137969 A1 | 5/2009 | Colantonio et al. |
| 2009/0205151 A1 | 8/2009 | Fisher et al. |
| 2010/0000040 A1 | 1/2010 | Shaw et al. |
| 2010/0047123 A1 | 2/2010 | Solomon et al. |
| 2010/0050351 A1 | 3/2010 | Colantonio et al. |
| 2010/0172794 A1 | 7/2010 | Ferlic et al. |
| 2010/0174162 A1 | 7/2010 | Gough et al. |
| 2010/0199448 A1 | 8/2010 | Vazales et al. |
| 2010/0312197 A1 | 12/2010 | Sano et al. |
| 2010/0313366 A1 | 12/2010 | Rogers et al. |
| 2011/0213341 A1 | 9/2011 | Solomon et al. |
| 2011/0265825 A1 | 11/2011 | Rogers et al. |
| 2011/0277788 A1 | 11/2011 | Rogers et al. |
| 2012/0039764 A1 | 2/2012 | Solomon et al. |
| 2013/0019421 A1 | 1/2013 | Rogers et al. |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 | 9/1995 |
| JP | 09-206370 A | 8/1997 |
| JP | 09-012829 U | 9/1997 |
| JP | 2001-527441 A | 12/2001 |
| JP | 2002-291906 A | 10/2002 |
| JP | 4234777 B1 | 3/2009 |
| WO | WO-94/11474 A1 | 5/1994 |
| WO | WO-98/48872 A1 | 11/1998 |
| WO | WO-00/24442 A1 | 5/2000 |
| WO | WO-2007/103998 A2 | 9/2007 |
| WO | WO-2007137056 A2 | 11/2007 |
| WO | WO-2009/136957 A1 | 11/2009 |
| WO | WO-2009/153224 A1 | 12/2009 |

(56) References Cited

FOREIGN PATENT DOCUMENTS

| WO | WO-2011/056221 A1 | 5/2011 |
|---|---|---|
| WO | WO-2011/120017 A1 | 9/2011 |

OTHER PUBLICATIONS

U.S. Appl. No. 60/832,437, filed Jul. 21, 2006, Rogers.
Byington "Spontaneously Generating Life in Your Classroom? Pasteur, Spallanzani & Science Process," *The American Biology Teacher*, vol. 63, No. 5 (May 2001). pp. 340-345. Published by University of California Press on behalf of National Association of Biology Teachers.
European Patent Office, Supplementary Partial European Search Report and Opinion for EP Application No. 07 75 8117 date of completion of the search Nov. 22, 2012, 6 pgs.
International Search Report and Written Opinion dated Nov. 9, 2012, PCT/US2012/025517.
International Standard ISO 594-2. "Conical Fitting with 6% (Luer) Taper for Syringes, Needles and Certain Other Medical Equipment— Part 2: Lock Fittings". Reference No. ISO 594-2:1998(E). Second edition. (Sep. 1, 1998)1:11.
Japanese Patent Office, Japanese Notice of Reasons for Rejection for Japanese Patent Application No. 2008-558527 dated Apr. 12, 2012.
Japanese Patent Office, Japanese Notice of Reasons for Rejection for Japanese Patent Application No. 2008-558527 dated Apr. 2, 2013.
Material Properties of Polyamide (Nylon), www.madeitfrom.com, pp. 1-2. [Retrieved Sep. 23, 2012].
Material Properties of Polycarbonate, www.madeitfrom.com, pp. 1-3. [Retrieved Sep. 23, 2012].
Material Properties of Polypropylene, www.madeitfrom.com, pp. 1-2. [Retrieved Sep. 23, 2012].
Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of The Society for Healthcare Epidemiology of America. Infect Control Hosp Epidemiol* vol. 27(2006):23-27.
Menyhay Healthcare Systems LLC available at http://www.menyhaymedical.comimenyhay.html [retrieved Nov. 8, 2013].
PCT Search Report and Written Opinion dated Oct. 16, 2013 for PCT application No. PCT/US2013/044167.
The International Bureau of WIPO, PCT International Preliminary Report on Patentability and Written Opinion of the International Searching Authority for International Application No. PCT/US2007/063534 dated Nov. 21, 2007.
Value Plastics Inc, Luer Connectors, http://www.valueplasctics.com/search/search.aspx, pp. 1-2. Retrieved Sep. 23, 2012.
Image File History for Re-examination Control No. 90/009,950.
Image File History for Re-examination Control No. 90/009,951.
Image File History for Re-examination Control No. 95/002,085.
Image File History for Re-examination Control No. 95/002,086.
Image File History for Re-examination Control No. 95/002,087.
PCT Form ISA 220, PCT NotificatiOn of Transmittal of the International Search Report and Written Opinion of the International Searching Authority, dated Jul. 22, 2009, issued in connection with corresponding PCT Application PCT/US2008/053744.
European Patent Office, European Search Report and Opinion for EP Application No. EP 10 78 3956, date of completion of the search Mar. 12, 2014, 7 pgs.
International Search Report and Written Opinion issued in International Application No. PCT/US2014/026716, mailed Jun. 12, 2014.

MEDICAL IMPLEMENT CLEANING DEVICE

CROSS REFERENCE TO RELATED APPLICATIONS

This application is a continuation of U.S. patent application Ser. No. 13/466,976 filed on May 8, 2012, entitled, "Medical Implement Cleaning Device," which is a continuation of U.S. patent application Ser. No. 13/189,457 filed on Jul. 22, 2011, issued on Jun. 26, 2012 as U.S. Pat. No. 8,206,514, and entitled, "Medical Implement Cleaning Device," which is a continuation of U.S. patent application Ser. No. 12/860,825 filed on Aug. 20, 2010, issued on Jul. 26, 2011 as U.S. Pat. No. 7,985,302, and entitled "Medical Implement Cleaning Device," which is a continuation of U.S. patent application Ser. No. 11/705,805 filed on Feb. 12, 2007, issued on Aug. 24, 2010 as U.S. Pat. No. 7,780,794, and entitled "Medical Implement Cleaning Device," which claims the benefit under 35 U.S.C. §119(e) of U.S. Provisional Patent Application Ser. No. 60/832,437 filed on Jul. 21, 2006 and entitled "Disinfecting Cap" and also claims the benefit under 35 U.S.C. §119(e) of U.S. Provisional Patent Application Ser. No. 60/850,438 filed on Oct. 10, 2006 and entitled "Disinfecting Cap." The disclosures of all applications to which the current application claims priority are incorporated by reference herein in their entireties.

BACKGROUND

Within the medical field, and in particular the area of infusion of fluids or aspiration of fluids to or from a patient, there is a need to prevent the transmission of pathogens into or onto a patient from a potentially contaminated surface of a medical implement, or "site". Such pathogens include microorganisms such as bacteria and viruses. The transmission of pathogens into a patient may result in an infection that could be life threatening. Specific to healthcare settings, the term "nosocomial infection" describes those infections that originate from or occur in a hospital or hospital-like setting. In the U.S., nosocomial infections are estimated to occur in at least 5% of all acute care hospitalizations. The estimated incidence is more than two million cases per year, resulting in an added expenditure in excess of $4.5 billion. Nosocomial infections are estimated to more than double the mortality and morbidity risks of any admitted patient, and likely result in about 90,000 deaths a year in the United States. Common sites for such transmissions are found on such medical implements as a luer port, vial, needle free valve, or an injection port of a vessel, tubing, or catheter. Even non-intrusive medical implements such as stethoscopes can transmit pathogens to a patient. The incidence of infection in patients is presently numerous and increasing, and Infection Control Practitioners (ICP's) often cite improper cleaning of sites as a major source of these infections.

Traditionally, cleaning a potentially contaminated surface includes a protocol of alcohol swabbing prior to making the necessary connections to the site. Today alcohol swabs, a small pad of cotton gauze soaked in isopropyl alcohol, are packed individually in a foil package. The foil package is relatively inexpensive, and is used to retain the alcohol within the package and to prevent evaporation. Properly used, the package is opened at or near the site to be swabbed. With gloved hands, the pad is removed by a healthcare provider and wiped across the top and side surfaces of the site, and the pad and foil package are discarded. The site should be allowed to dry, usually twenty to thirty seconds, immediately prior to making any connection. This "drying" period is important: when alcohol dries, it breaks open the cellular walls of microorganisms, thereby killing them.

Unfortunately, because of increased duties and responsibilities, shrinking nursing staffs, and inadequate training, swabbing is often overlooked or is poorly executed. A poorly swabbed site can carry microorganisms that, if allowed to enter a patient's body, can cause serious infection. In addition, supervisory oversight is nearly impossible, because unless a supervisor can actually observe the swabbing being performed, the supervisor cannot know whether or not it was done properly or performed at all. Further, without at least a sufficient microscopic examination for microbial residue, there may be no evidence of an alcohol swab being performed. Thus, a need exists for an apparatus and technique for cleaning a site on a medical implement prior to contact with a patient, and which will eliminate technique-related issues and training issues, and provide an unequivocal indicator that a site is clean prior to accessing a patient's vascular system.

SUMMARY

A cleaning device, system and method for a medical environment is disclosed. In one aspect, the system includes a strip of flexible material and a plurality of cleaning devices attached to the strip of flexible material. Each of the plurality of cleaning devices includes a cap that is selectively removable from the strip of flexible material. The cap includes an inner cavity that is sealed when the cleaning device is attached to the strip of flexible material and configured to be unsealed upon removal of the cleaning device from the strip of flexible material. The inner cavity receives a site of the medical implement. Each of the plurality of cleaning devices further includes one or more protrusions that extend inwardly from the inner cavity. The one or more protrusions engage corresponding protrusions on the site of the medical implement to maintain the cap on the site of the medical implement after the site of the medical implement is received into the inner cavity of the cap. Each of the plurality of cleaning devices further includes a cleaning agent that occupies at least some of the inner cavity. The cleaning agent is formulated to clean the site of the medical implement as the inner cavity of the cap receives the site of the medical implement and when the cap is maintained on the site of the medical implement.

The above system can, in some implementations, further include one or more of the following features.

Each of the plurality of cleaning devices can further include at least one aperture to the inner cavity after the site of the medical implement is received into the inner cavity of the cap. The at least one aperture can be configured to release pressure in the inner cavity of the cap as the inner cavity of the cap receives the site of the medical implement.

The at least one aperture can be further configured to allow evacuation of at least some of the cleaning agent from the inner cavity when the inner cavity of the cap receives the site of the medical implement.

The strip of flexible material can include at least one hole.

The inner cavity of the cap of each of the plurality of cleaning devices can be sealed by the strip of flexible material before the cleaning device is removed from the strip of flexible material.

In another aspect, a system for cleaning a site of a medical implement includes a plurality of cleaning devices. Each of the plurality of cleaning devices includes a cap having an inner cavity for receiving a site of the medical implement. Each of the plurality of cleaning devices further includes one or more protrusions that extend inwardly from the inner cavity. The one or more protrusions engage corresponding protrusions on the site of the medical implement to maintain the cap on the site of the medical implement after the site of the medical implement is received into the inner cavity of the cap. Each of the plurality of cleaning devices further includes a cleaning agent that occupies at least some of the inner cavity. The cleaning agent is formulated to clean the site of the medical implement as the inner cavity of the cap receives the site of the medical implement and when the cap is maintained on the site of the medical implement. Each of the plurality of cleaning devices further includes a removable seal that seals the cleaning agent within the inner cavity prior to the inner cavity of the cap receiving the site of the medical implement. The system further includes a strip of flexible material attached to the plurality of cleaning devices. Each of the plurality of cleaning devices can be individually removed from the strip of flexible material.

The above system can, in some implementations, further include one or more of the following features.

Each of the plurality of cleaning devices can further include at least one aperture to the inner cavity after the site of the medical implement is received into the inner cavity of the cap. The at least one aperture can be configured to release pressure in the inner cavity of the cap as the inner cavity of the cap receives the site of the medical implement.

At least one aperture can be further configured to allow evacuation of at least some of the cleaning agent from the inner cavity when the inner cavity of the cap receives the site of the medical implement.

The strip of flexible material can include at least one hole.

The inner cavity of the cap of each of the plurality of cleaning devices can be sealed by the strip of flexible material before the cleaning device is removed from the strip of flexible material.

In yet another aspect, a cleaning system for a medical connector having an access site includes a strip of material having at least one hole. The cleaning system further includes a plurality of cleaning devices. Each cleaning device is removably attached to the strip of material. Each cleaning device includes a cap having an inner cavity for receiving the access site of the medical connector upon removal from the strip of material. The inner cavity is sealed when the cap is attached to the strip of material. Each cleaning device further includes one or more protrusions that extend inwardly at least partially around an inside surface of the inner cavity of the cap. The one or more protrusions engage an outer surface of the access site of the medical connector to maintain the cap on the access site of the medical connector when the cap is removed from the strip of material. Each cleaning device further includes a cleaning agent that occupies at least some of the inner cavity of the cap. The cleaning agent is formulated to clean the access site of the medical connector when the opening of the cap receives the access site of the medical connector.

The above cleaning system can, in some implementations, further include one or more of the following features.

The one or more protrusions can include threading.

In yet another aspect, a cleaning system for a medical implement includes a plurality of caps. Each of the plurality of caps includes an inner cavity that receives a site of the medical implement into the inner cavity. Each of the plurality of caps further includes a cleaning material in the inner cavity that is adapted to provide axial compression against the site of the medical implement. The cleaning material contains a cleaning agent prior to receipt of the site of the medical implement into the inner cavity. The cleaning agent is adapted to clean the site of the medical implement. Each of the plurality of caps further includes threading in the inner cavity near the opening to the cap. The threads correspond to threads on the medical implement. The cleaning system further includes a strip attached to the plurality of caps, and from which individual caps of the plurality of caps can be selectively removed to be used for cleaning the site of the medical implement.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1:
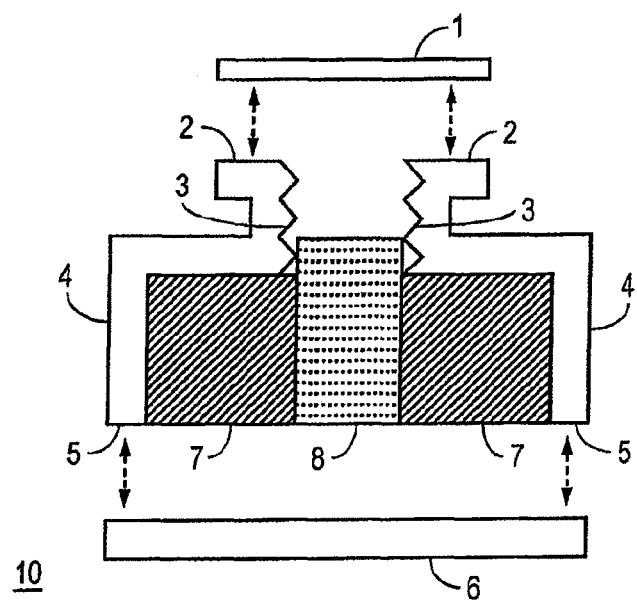
FIG. 1 is a cross-sectional, exploded view of a cleaning device.

In accordance with preferred embodiments, a cleaning device includes a cap having a shape and/or external features to promote easy gripping and a cleaning material in the cap that holds or is in contact with a cleaning agent, such as isopropyl alcohol, for application of the cleaning agent to a site of a medical implement.

The cleaning material can be any substance that can conform, mold or compress in a manner that enables the effective wiping of the site, including the top surface of the site, side surface, and any threads or grooves, if present, and provide the cleaning agent at least at a surface level. Examples of the cleaning material include cotton, open or closed cell foam such as polyethylene foam, or other substance that can hold or carry the cleaning agent. The cleaning agent can be any chemical, substance or material that cleans the site of bacterial or even viral microorganisms, or any carrier that contains such chemical, substance or material. Examples of a cleaning agent include isopropyl alcohol, chlorhexidine, povidone-iodine, hydrogen peroxide, soap, and hydrochloric acid.

The term "medical implement" is used to denote any tool or object that can be used in a medical setting and that can connect to a site cleaning device as described herein according to a number of embodiments. Examples of medical implements include, but are not limited to, access ports on tubing sets (extension sets, T-connectors and IV sets), access ports on catheters (both peripheral and central lines), needle free valves, stopcocks, luer connectors, stethoscopes and other components or devices whereby regular cleaning is desired. Medical implements are commercially available in standard sizes. Thus, the end or opening of a site cleaning device can be provided with fittings to accommodate such standard size medical implements.

The cap of the cleaning device is made of a material that is compatible with the cleaning materials and agents to be used, examples of materials would include, sealed foam, plastic, glass, or metal. The cleaning device may need to undergo sterilization. For securing the cleaning device to another device, the cleaning device can include attachment mechanisms such as "snap-fit" mechanisms or clamps to hold it in place on the other device. Alternatively the cleaning material in the cap may conform to the sides of the medical implement to thereby "grip" and remain secured to the medical implement. The cap also may have threading to secure it in place on a medical implement. The cap may have some cutaway portions on its walls to enable the use of some undercuts during the molding process, and to allow the cleaning material to flex outward both during use. The cap can be made from polyethylene or another material that is stable when in the presence of alcohol or other cleaning agent.

In preferred exemplary embodiments, prior to being applied to a site, and after the cleaning material is provided with a cleaning agent, the opening of the cap is sealed with a foil-based seal or other material suitable for retaining a cleaning agent in the cleaning material and preventing evaporation of the cleaning agent. The cap seal may also be formed in a manner whereby several caps could be attached i.e. a strip, where individual caps can be peeled from the strip in order to be used. These strips of caps can be made conveniently accessible, i.e. hung from intravenous (IV) poles or IV sets, in patient rooms and medication carts, to name just a few. The strips provide the convenience of having several caps available in one location.

The cleaning material in the cap can be an alcohol-soaked piece of gauze, foam or similar cleaning material. The cleaning material can be formed into the general interior shape of the cap from one or more pieces. For instance, the cleaning material can include a ring for circumscriptive coverage and cleaning of the site, and further include a cylinder within the ring for coverage and cleaning on a distal end of the site. A single piece of cleaning material may also be cut or formed to perform the same coverage and cleaning functions as the two pieces described above. The cleaning material may also cover the threads and/or be formed as part of the threads.

In still further embodiments, the cleaning material may be made entirely or partially of the cleaning agent. For example, the cleaning material can be formed of an open cell foam or plastic that is chemically or physically impregnated with a cleaning agent such as povidone or iodine, or isopropyl alcohol.

To further illustrate and describe these concepts, reference is now made to FIG. 1, which shows a cross-sectional, exploded view of a cleaning device, embodied as a cap 10 with a housing 4 that defines an inner cavity 20 of the cap 10. A foil seal 1 is configured to attach to a sealing surface 2 of the housing 4. The housing 4 further includes internal threads 3. In a preferred exemplary embodiment, the internal threads 3 are sized and arranged to accommodate luer threads, i.e. standardized male threads designed to mate with the female threads on a medical implement to which the cap 10 attaches. The housing 4 also has a mating surface 5 for attachment of a bottom portion 6.

Within housing 4 is a first cleaning material 7. The first cleaning material 7 may be attached to the walls of housing 4 by glue, solvent or some other attachment composition or mechanism, or may be held in the housing 4 by compression or trapped between the bottom portion 6 and housing 4. Ribs or protrusions on the inside of the housing 4 may also be used to prevent the cleaning material 7 from slipping or rotating. The first cleaning material 7 is compressible, and is preferably doughnut-shaped or ring-shaped. The first cleaning material 7 is positioned and configured to compress radially in an outwardly direction to scrub or wipe the circumscriptive surface of the site and the surface of the threads of an inserted medical implement.

A second cleaning material 8 is designed to compress in the axial direction upon insertion of the medical implement and is designed to wipe the distal end and distal surface of the inserted medical implement. The second cleaning material 8 may be attached to the walls of bottom portion 6 by glue, solvent or some other attachment composition or mechanism, or affixed to first material 7 by glue, solvent or some other attachment composition or mechanism. Protrusions on the inside of the bottom portion 6 may also be used to prevent the cleaning material 8 from rotating or removal. The first cleaning material 7 and second cleaning material 8 may be formed from a single piece of compressible cleaning material of cotton, foam or other suitable cleaning material adapted for scrubbing. This single piece may be cut completely or partially cut to achieve a similar effect as two separate pieces of cleaning material.

Figure 2:
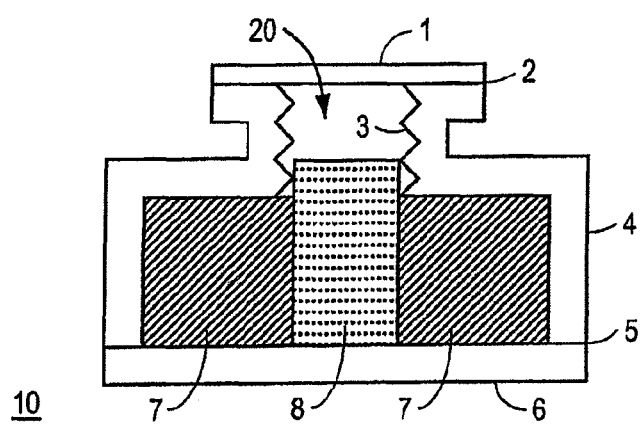
FIG. 2 is a cross-sectional view of an assembled cleaning device.

FIG. 2 illustrates an assembled cap 10. The first and second cleaning materials 7 and 8 in the inner cavity 20 are at least partially saturated with a cleaning agent, such as isopropyl alcohol, or a mix of cleaning agents. The foil seal 1 is then attached to housing 4 at sealing surface 2 by glue, solvent, thermal bonding, etc. A bottom portion 6 is attached to housing 4 at point 5 by glue, welding, solvent, threads or other attachment mechanism or process. With the foil seal 1 and the bottom portion 6 attached to housing 4, the inner cavity 20 is hermetically sealed. The housing 4, bottom portion 6, and first and second cleaning materials 7, 8 are respectively made of a material or cleaning materials that are compatible with the cleaning agent. For instance, if isopropyl alcohol is used for at least part of the cleaning agent, the housing 4 and bottom portion 6 can be constructed of a plastic such as polyethylene. The housing 4 and bottom portion 6 can be formed of a unitary piece of material, as explained further below.

Figure 3:
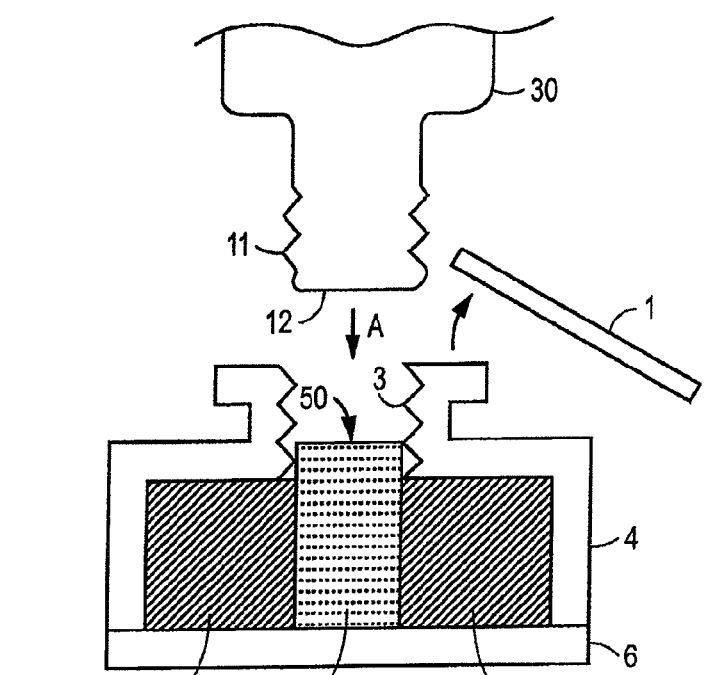
FIG. 3 illustrates operation of a cleaning device for connection to a site of a medical implement.

FIG. 3 illustrates a medical implement 30 moving toward housing 4, in a direction A, which should be recognized as a reference only, and that the housing 4 can likewise be moved toward the medical implement 30. The foil seal 1 is removed from housing 4. In alternative embodiments, the foil seal 1 can be a foil pouch or other sterilized material that would inhibit evaporation of the cleaning agent. A distal end surface 12 of the medical implement 30 is eventually contacted with the upper surface 50 of the second cleaning material 8.

Figure 4:
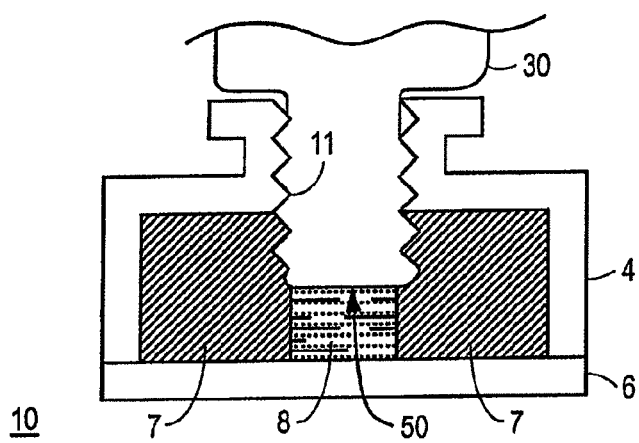
FIG. 4 illustrates a cleaning device connected to a medical implement and cleaning a site of the medical implement.

As the medical implement 30 continues in direction A, it axially compresses second cleaning material 8 continuing to clean surface 12 with surface 50. This movement also begins to radially compress the first cleaning material 7 and to conform the first cleaning material 7 with, and begin scrubbing, threads 11. The cleaning materials 7 and 8 contain the cleaning agent so as to perform a thorough cleaning of the area about the threads 11 and the surface 12. As threads 11 of the medical implement 30 continue to be rotationally inserted into the threads 3 of the housing, the distal end surface 12 is automatically scrubbed by surface 50 of the second cleaning material 8 and cleaned by cleaning agent held therein, and at least a portion of the side and threads 11 of the medical implement 30 are automatically scrubbed by radial compression of the first cleaning material 7 and cleaned by a cleaning agent held therein. FIG. 4 illustrates the disinfecting cap 10 with a fully inserted medical implement 30.

The cap 10 can be removed immediately from the medical implement 30 after use, or be kept in place. If the cap 10 is removed the medical implement 30 surfaces 11 and 12 will be clean and ready for use upon the drying of the cleaning agent. If the cap 10 is kept secured to medical implement 30, the cleaning agent in cap 10 will evaporate over time thereby destroying any microorganisms on the surfaces 12 and 11 of medical implement 30. The cap 10 then maintains the surfaces 11 and 12 of medical implement 30 in a clean and ready-to-access state by eliminating any forms of touch contamination.

Figure 5:
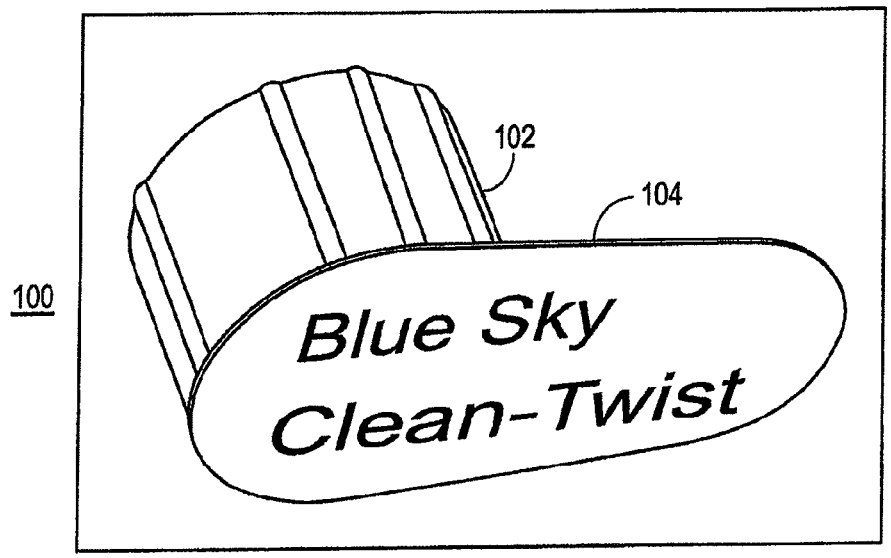
FIG. 5 shows another embodiment of an assembled cleaning device.
Figure 6:
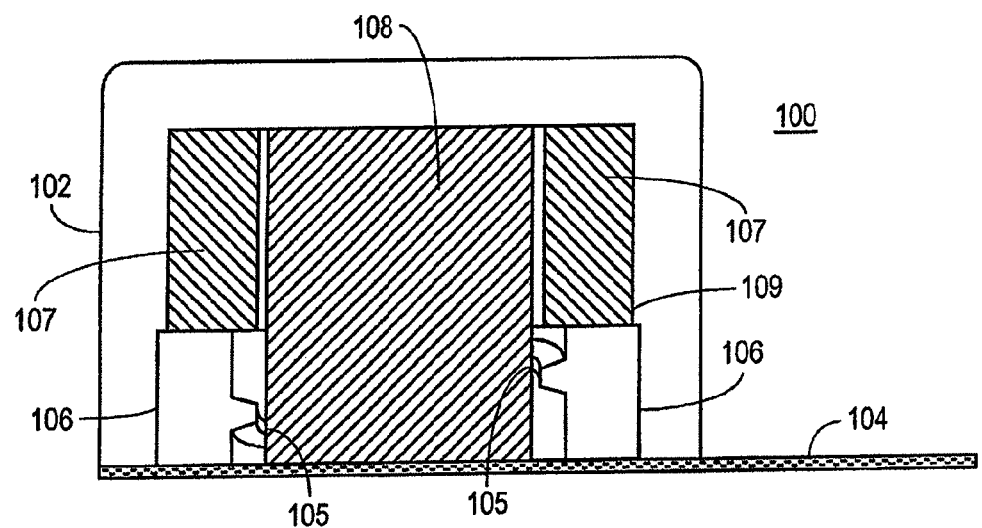
FIG. 6 is a cross-sectional view of an assembled cleaning device in accordance with an embodiment.

FIGS. 5-10 illustrate an alternate embodiment of a cleaning device 100. FIG. 5 is a perspective view of the cleaning device 100 formed of a cap 102 with a seal 104 that is connected to and covers the opening of the cap 102. The cap 102 can have a number of gripping ridges or projecting members for ease of use. FIG. 6 is a cross-sectional view of the cleaning device 100. The cap 102 forms an inner cavity with one opening that is large enough to receive a site of a medical implement. The seal 104 is affixed to the opening and is preferably entirely removable. In other embodiments, the seal 104 is permanently affixed, and is simply punctured by insertion of a site of a medical implement.

The cap 102 houses a threaded ring 106 proximate to the opening. The threaded ring 106 includes one or more threads 105 and is adapted to receive the site of the medical implement to be disinfected, and thus defines the size and shape of the opening. This embodiment is advantageous because it creates a single circumferential seal point, seal 104 to the opening of cap 102.

In some embodiments, the cap 102 and threaded ring 106 are formed of a unitary piece of material or cleaning material. In other embodiments, the threaded ring 106 fits into a groove 109 that is formed in the inside edge surface of the cap 102 near the opening. In this latter configuration, the groove 109 maintains the position of threaded ring 106 near the open end of the cap where the threaded ring top surface may be flush with or slightly recessed from the cap open end walls, and the threaded ring 106 may also include or create with the cap wall a small vent aperture or opening to allow evaporation of a cleaning agent in the cap 102. The threaded ring 106 can be mechanically kept from rotating with internal ribs or protrusions in cap 102 or groove 109. Threaded ring 106 may be held in place within grove 109 and cap 102 by glue, welding, snap-fit, solvent bonding or any other mechanism or composition known to those of requisite skill.

The cleaning device 100 further includes a first cleaning material 107 that holds the cleaning agent, such as isopropyl alcohol, and a second cleaning material 108 that also holds or is at least partially saturated by the cleaning agent. In preferred exemplary embodiments, the first cleaning material 107 is formed as a hollow cylinder or ring positioned between the threaded ring 106 and the top inside surface of the cap 102, and is adapted for radial compression against a site that is inserted into the cap 102 or over which the cap 102 is placed. In some embodiments, the second cleaning material 108 is formed as a solid cylinder and positioned within the hollow space of the first cleaning material 107, and is adapted for axial compression against a leading edge of the site that is inserted into the cap 102 or over which the cap 102 is placed. In other embodiments, cleaning materials 107 and 108 can be made of a single piece of material and cut or formed so as to achieve the same result as described above. The cleaning agent is provided to the cleaning materials 107, 108 prior to the opening being covered with the seal 104.

Figure 7:
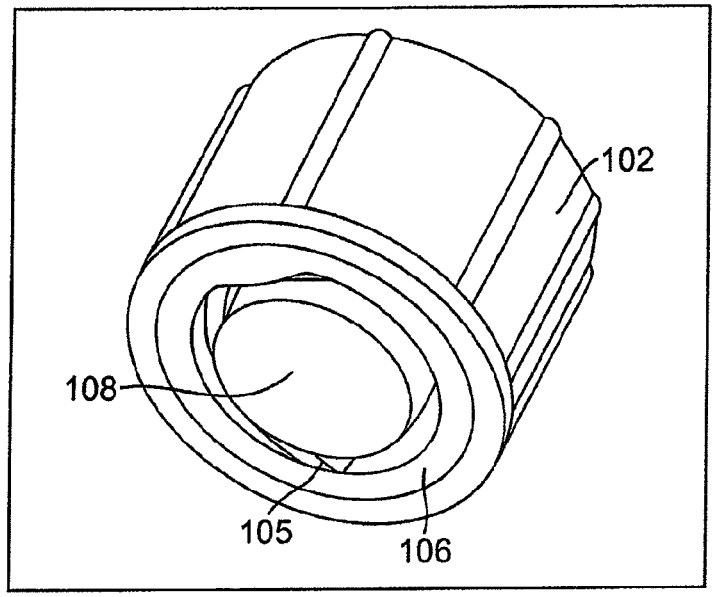
FIG. 7 is a perspective view of another cleaning device.
Figure 8:
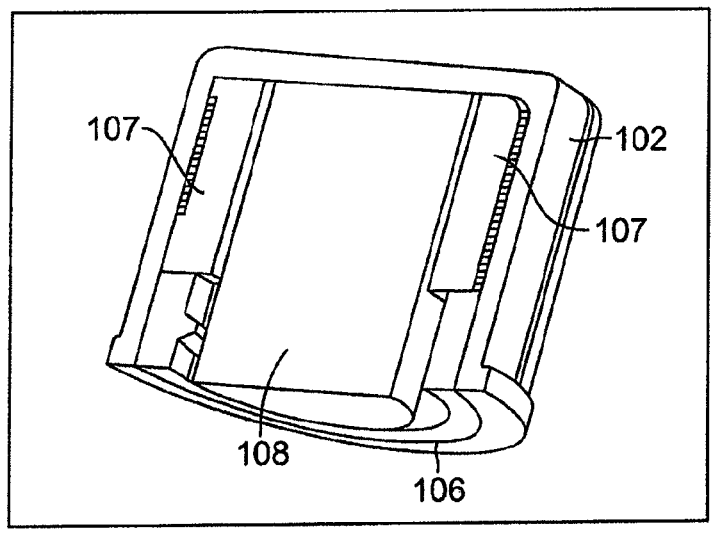
FIG. 8 is a cross section of a cleaning device.
Figure 11:
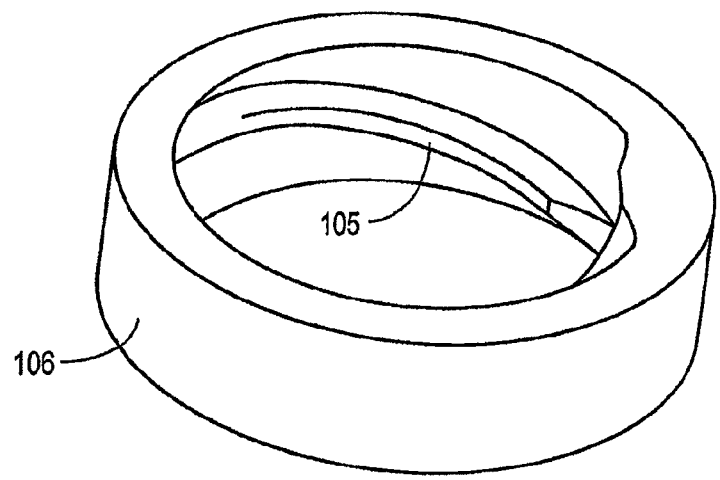
FIG. 11 is a perspective view of a ring that attaches to a corresponding structure of a medical implement.

FIG. 7 is a bottom perspective view and FIG. 8 is a cross-sectional view of the cleaning device 100 with the seal 104 removed, showing the cap 102, threaded ring 106 that sits within the cap 102, and the second cleaning material 108 inside the cap 102. The second cleaning material 108 can extend to and slightly beyond the opening of the cap 102. FIG. 8 further shows the first cleaning material 107 that circumscribes the second cleaning material 108 and being positioned between the threaded ring 106 and the top inner surface of the cap 102. FIG. 11 illustrates an example of the threaded ring 106 and its threads 105. An attribute of this embodiment of the threaded ring 106 shown in FIG. 11 is that there are only two opposing threads that travel 180 degrees before terminating. This enables the molding of threaded ring 106 without the use of a screw to create the thread feature in an injection molding tool. The threaded ring 106 can also be produced with an injection molding tool utilizing a screw.

Figure 9:
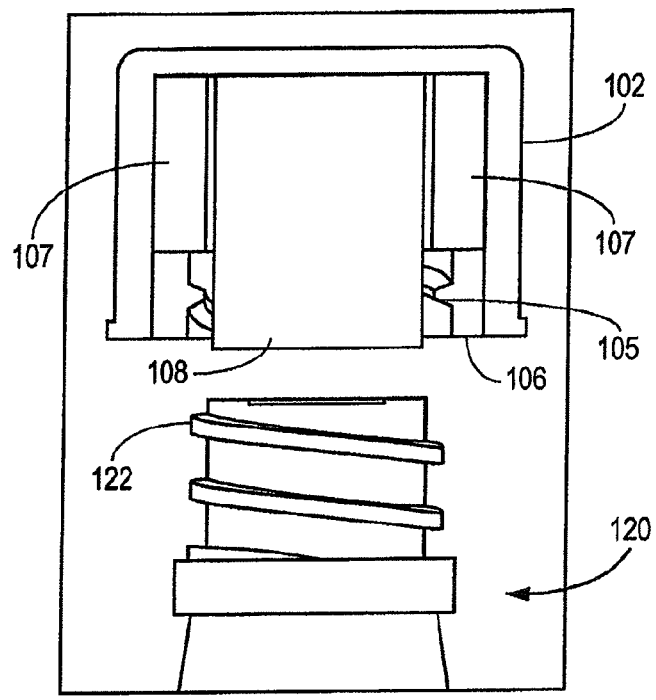
FIGS. 9 and 10 show a cleaning device being used to clean a site of a medical implement.
Figure 10:
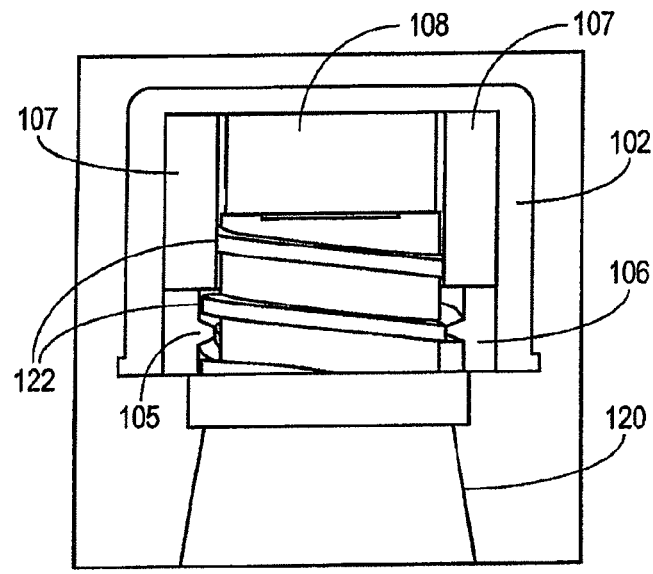

FIG. 9 illustrates the cleaning device 100 about to make contact with a site 120 of a medical implement. As discussed above, the site 120 can be a luer port, a, a needle free valve, an injection port of a vessel, or other medical implement that needs to be cleaned prior to use with a patient. In some embodiments, the site 120 can include a set of threads 122 that correspond to the threads 105 in the threaded ring 106 of the cleaning device 100. The cleaning materials 107 and 108 are preloaded with a cleaning agent, before removal of the seal and contact by the site 120. Accordingly, as shown in FIG. 10, the site 120 makes contact with the cap 102 by a screwing motion relative to the cap 102. The second cleaning material 108 is compressed axially and swabs against the leading edge of the site 120, while the first cleaning material 107 is compressed radially and swabs against sides of the site 120.

FIG. 11 illustrates the molded thread ring 106 with two opposing threads 105 that traverse opposing 180 degree portions of the ring. This design enables the thread ring 106 to be molded without the use of a screw that is typically used to create threaded parts in a molding process. Thus the threaded ring 106 can be manufacture very inexpensively. The threaded ring 106 can also clean some of the threads when the cap is placed into position, and may or may not cover all the threads. In some embodiments, the threaded ring 106 can be molded from the cleaning material, or the cleaning material is formed only of the threaded ring 106. In such embodiments, the cleaning may only occur on threads of the site and in an axial direction.

Figure 12:
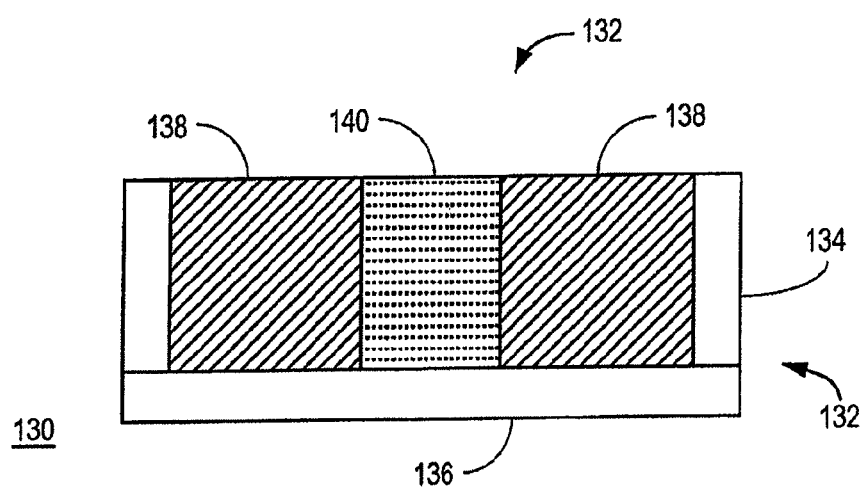
FIG. 12 is a cross sectional view of another alternative embodiment of a cleaning device.

FIG. 12 shows an alternative embodiment of a cleaning device 130 having a cap 132 that is filled with a cleaning material. The cap 132 has side walls 134 and a top 136 that define an inner cavity with an opening 132. The cleaning material includes at least a first cleaning material 138, such as cotton or foam, that delivers a cleaning agent. The cleaning material can include a second cleaning material 140 to hold more cleaning agent. In some embodiments, the second cleaning material 140 can be circumscribed by the first cleaning material 138. Alternatively, the first cleaning material 138 can completely envelope the second cleaning material 140, each providing their own compressibility and capacity to hold a cleaning agent. Still, in other embodiments, the first and second cleaning materials 138, 140 can be formed of a single piece of material. The cleaning material(s) are filled at least partially with a cleaning agent, prior to sealing of the opening 132 with a seal and closure of the inner cavity.

Figure 13:
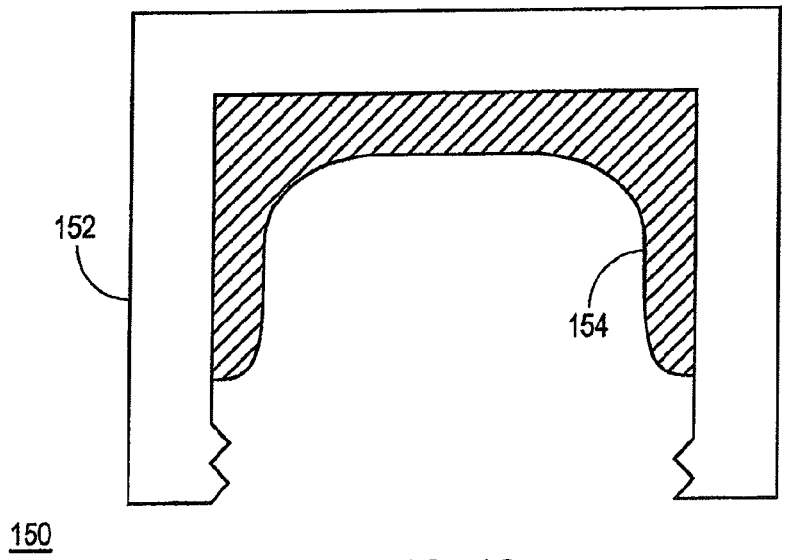
FIG. 13 shows yet another alternative embodiment of a cleaning device.

FIG. 13 shows an alternate embodiment of a cleaning device 150. In this embodiment, the cleaning device 150 includes a housing 152 that is formed as a threaded cap. The inner surface of the housing 152 is covered, at least in part, by a cleaning layer 154 that is bonded to the inner surface of the housing 152. The cleaning layer 154 can be a cleaning material such as cotton, foam, or other porous and pliable material that suitably holds and/or delivers a cleaning agent such as isopropyl alcohol. The cleaning layer 154 is sized and positioned inside the housing 152 so as to be able to swab the top and a portion of the sides of a part of a medical implement that is inserted therein, or over which the housing 152 is placed. Accordingly, the cleaning layer 154 can have any thickness or compressibility.

Figure 14:
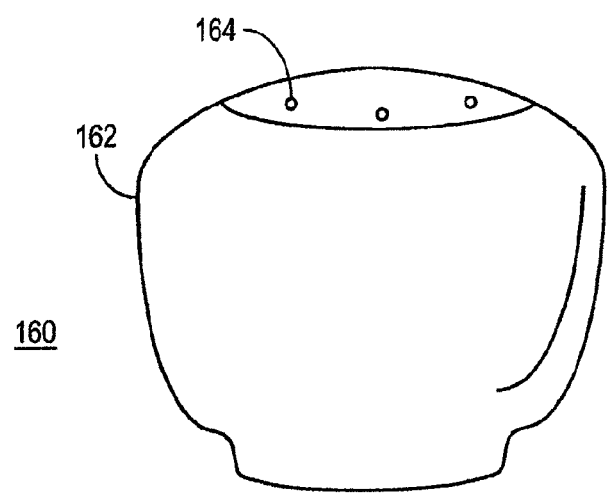
FIG. 14 shows a cap of a cleaning device in accordance with some embodiments.

FIG. 14 shows yet another alternative embodiment of a cleaning device 160, illustrating an outer view of a rounded housing 162 for an expanded inner chamber to hold more cleaning agents or cleaning materials that hold such agents. Holes 164 in the housing 162 can promote evaporation of the cleaning agent, particularly when the housing covers a site of a medical implement to be disinfected. The location of the vent holes is variable and the vent holes can also be sealed with a filter type membrane that permits the drying of the cleaning agents but does not allow entry of microorganisms or fluid.

The use of the various implementations and embodiments above entails the following: the healthcare worker would, with gloved hands, open the foil package and place this cap over the site of a medical implement to be cleaned. Upon placement the alcohol soaked cleaning material wipes all of the port's surfaces. This wipe could be accomplished by either a turning motion (if threads are used) or by simply pushing the cap onto the port. In this way the cap eliminates errors in the practice of swabbing due to poor training or excessive workloads. The cap would then remain secured in place by threads, mechanical tension provided by the foam, cotton, etc., snaps or some other mechanism. A cap in place on a medical implement is a positive indication that a desired site of the medical implement is clean. A vibrant color may be used to allow instant visualization of a cap's presence from a door or hallway. ICP's can review compliance by merely observing sites to see whether or not a cap is in place. The cap could remain in place for periods of up to three days or more. For extended periods the alcohol will likely evaporate, which assures that the site is clean. With the cap in place, it continues to keep the site clean even after the alcohol has evaporated.

Although a few embodiments have been described in detail above, other modifications are possible. For instance, any of the embodiments described above may be sized and scaled for a particular medical implement, such as a stethoscope. Other embodiments may be within the scope of the following claims.

The invention claimed is:

1. A system for cleaning a site of a luer activated valve (LAV), the system comprising:
   a strip of material; and
   a plurality of cleaning devices attached to the strip of material, each of the plurality of cleaning devices comprising:
      a cap that is selectively removable from the strip of material, the cap having an inner cavity, the inner cavity being sealed when the cleaning device is attached to the strip of material and configured to be unsealed upon removal of the cleaning device from the strip of material, the inner cavity for receiving a site of the LAV;
      one or more protrusions extending inwardly from the inner cavity, the one or more protrusions to engage corresponding protrusions on the site of the LAV to maintain the cap on the site of the LAV after the site of the LAV is received into the inner cavity of the cap;
      a cleaning agent that occupies at least some of the inner cavity, the cleaning agent being formulated to clean the site of the LAV as the inner cavity of the cap receives the site of the medical implement and when the cap is maintained on the site of the LAV; and
      at least one aperture to the inner cavity when the site of the LAV is received into the inner cavity of the cap.

2. The system in accordance with claim 1, wherein the at least one aperture is further configured to allow evacuation of at least some of the cleaning agent from the inner cavity when the inner cavity of the cap receives the site of the one or more protrusions extending inwardly from the inner cavity, the one or more protrusions to engage corresponding protrusions.

3. The system in accordance with claim 1, wherein the inner cavity of the cap of each of the plurality of cleaning devices is sealed by the strip of material before the cleaning device is removed from the strip of material.

4. A system for cleaning a site of a luer activated valve (LAV), the system comprising:
   a plurality of cleaning devices, each of the plurality of cleaning devices comprising:
      a cap having an inner cavity for receiving a site of the LAV, the cap being formed to provide at least one aperture to the inner cavity of the cap when the site of the LAV is received into the inner cavity of the cap;
      one or more protrusions extending inwardly from the inner cavity, the one or more protrusions to engage corresponding protrusions on the site of the LAV to maintain the cap on the site of the LAV after the site of the LAV is received into the inner cavity of the cap; and
      a cleaning agent that occupies at least some of the inner cavity, the cleaning agent being formulated to clean the site of the LAV as the inner cavity of the cap receives the site of the LAV and when the cap is maintained on the site of the LAV; and
   a strip of material attached to the plurality of cleaning devices, and from which the each of the plurality of cleaning devices can be individually removed, each of the plurality of cleaning devices being sealed prior to removal from the strip of material to seal the cleaning agent within the inner cavity.

5. The system in accordance with claim 4, wherein the at least one aperture is further configured to allow evacuation of at least some of the cleaning agent from the inner cavity when the inner cavity of the cap receives the site of the LAV.

6. The system in accordance with claim 4, wherein the inner cavity of the cap of each of the plurality of cleaning devices is sealed by the strip of material before the cleaning device is removed from the strip of material.

7. A cleaning system for a medical connector having an access site, the cleaning system comprising:
   a strip of material; and
   a plurality of cleaning devices, each cleaning device being removably attached to the strip of material, each cleaning device comprising:
      a cap having an inner cavity for receiving the access site of the medical connector upon removal from the strip of material, the inner cavity being sealed when the cap is attached to the strip of material;

one or more protrusions extending inwardly at least partially around an inside surface of the inner cavity of the cap, the one or more protrusions to engage an outer surface of the access site of the medical connector to maintain the cap on the access site of the medical connector when the cap is removed from the strip of material;

a cleaning agent that occupies at least some of the inner cavity of the cap, the cleaning agent being formulated to clean the access site of the medical connector when the inner cavity of the cap receives the access site of the medical connector; and at least one aperture to vent the inner cavity of the cap when the site of the medical implement is received into the inner cavity of the cap.

8. The cleaning system in accordance with claim 7, wherein the one or more protrusions includes threading.

9. A cleaning system for a medical implement, the cleaning system comprising:

a plurality of caps, each of the plurality of caps comprising:
an inner cavity to receive a site of the medical implement into the inner cavity;

a cleaning material in the inner cavity adapted to provide axial compression against the site of the medical implement, the cleaning material containing a cleaning agent prior to receipt of the site of the medical implement into the inner cavity, the cleaning agent being adapted to clean the site of the medical implement;

threading in the inner cavity near the opening to the cap, the threads corresponding to threads on the medical implement; and at least one aperture to vent the inner cavity of the cap when the site of the medical implement is received into the inner cavity of the cap; and a strip attached to the plurality of caps, and from which individual caps of the plurality of caps can be selectively removed to be used for cleaning the site of the medical implement.

10. The system in accordance with claim 1, wherein the aperture is formed between the one or more protrusions extending inwardly from the inner cavity of the cap and the corresponding protrusions of the LAV.

* * * * *